United States Patent [19]

Ellison et al.

[11] Patent Number: Plant 6,624

[45] Date of Patent: Feb. 21, 1989

[54] ASPARAGUS PLANT NAMED JERSEY KNIGHT

[75] Inventors: J. Howard Ellison, Milltown; John J. Kinelski, Princeton, both of N.J.

[73] Assignee: Rutgers University, New Brunswick, N.J.

[21] Appl. No.: 77,523

[22] Filed: Jul. 6, 1987

[51] Int. Cl.[4] ..... A01H 5/00

[52] U.S. Cl. ..... Plt./89

[58] Field of Search ..... Plt./89

*Primary Examiner*—Robert E. Bagwill

*Attorney, Agent, or Firm*—Frank B. Robb

[57] ABSTRACT

A male asparagus plant having tolerance to rust (*Puccinia asparagi*), root rot (*Fusarium oxysporum*), crown rot (*Fusarium moniliforme*), with high quality spears produced and high yield with spear tips remaining tight even in hot weather and when the spear is long.

1 Drawing Sheet

1

This invention relates to asparagus plants and more particularly to a plant which we have designated for identification and use in the trade as "Jersey Knight", and in our records it is also identified as No. 277C×22-8.

This particular plant is one of the products of a very extensive research program which has been carried on for years and which has produced this plant among many others which have outstanding characteristics for commercial purposes and also for breeding purposes, the usual problems of asparagus known being those of (*Fusarium oxysporum*) or root rot, rust (*Puccinia asparagi*) and crown rot (*Fusarium moniliforme*).

It is always an objective of this kind to reduce the impact of those particular problems on the ultimate product particularly where this is a food and is of considerable value in the trade being grown only in certain areas and most productively therein.

One of the well known varieties which has been used as a basis for development of various asparagus cultivars is the Mary Washington variety which is unpatented, but is grown extensively.

The subject invention, our plant identified as Jersey Knight, is a definite improvement over Mary Washington and in fact over some of the other varieties which we have developed and is a valuable commercial plant, as will be understood from further consideration of the information supplied herein.

We have propagated Jersey Knight asexually by crown division and as an all male asparagus hybrid, found that it has tolerance to rust (*Puccinia asparagi*), root rot (*Fusarium oxysporum*), crown rot (Fusarium moniliforme) and also have found that it produces high yields of high quality spears which is after all the ultimate aim of any such program.

A very important aspect of this particular variety is the fact that in certain areas in New Jersey where standard disease susceptible cultivars will not grown profitably, the variety of this invention, produces spear tips which remain tight longer than those of the standard cultivars and do not open when the spear is long as some cultivar spears do in hot weather. Spears which have open tips are unmarketable and thus desirably not produced.

Figure 1:
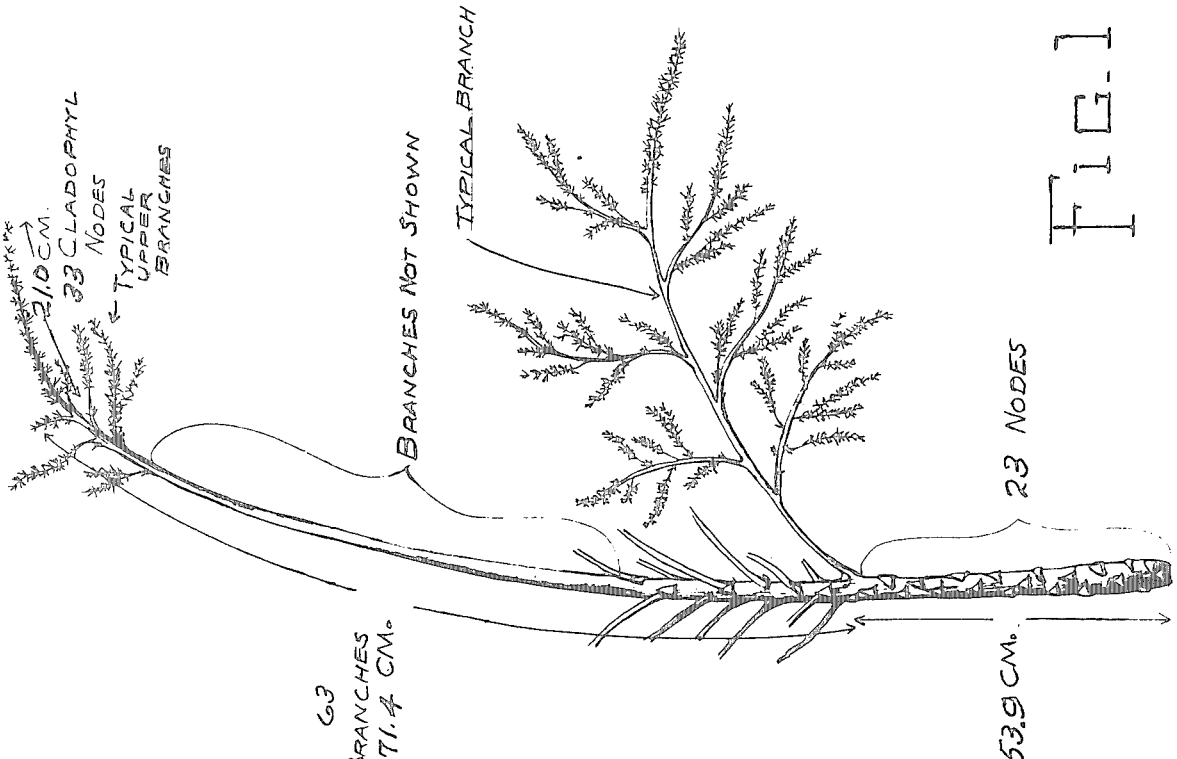

We have provided a drawing herein, wherein FIG. 1 shows a typical stalk of the plant, so that stalk data is applied thereto and summarized in a table to be noted

Figure 2:
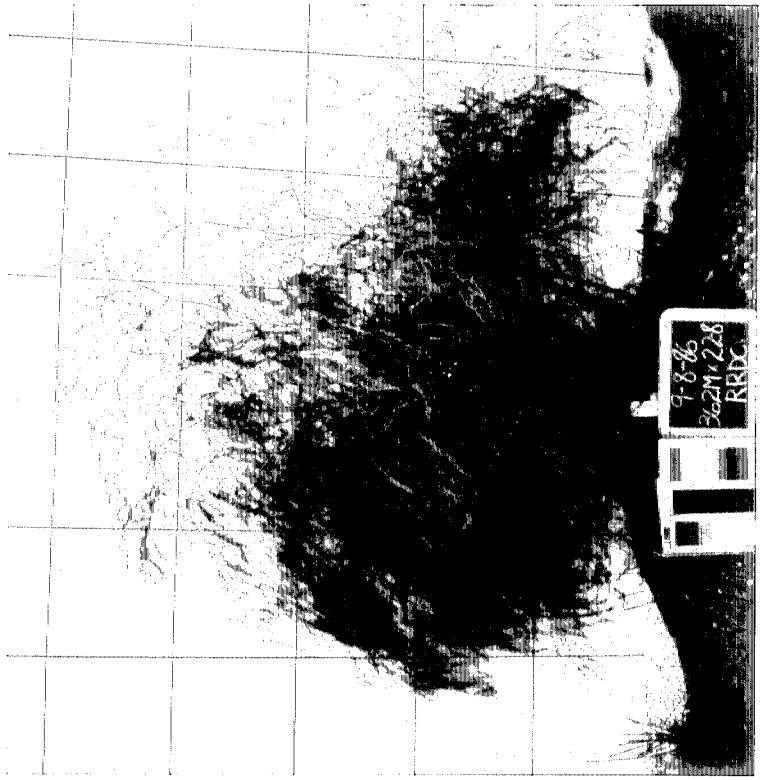

2 subsequently, and in FIG. 2 the color print of the variety as it ultimately grows and the plant is going to seed.

The color designations which are used in the data supplied, are those found in the Munsell Limit Color Cascade and are as nearly defined thereby as is possible in a color reproduction of this character, the color designations derived from comparison and viewing in normal daylight.

Among the important improvements provided by our new variety is the comparison provided by rust ratings and they are set forth in the table supplied, on the basis of a scale from one to nine in which nine indicates the most healthy of the same and the least rusty.

From this it will be observed that for the Mary Washington variety which is one of the control varieties, a rust rating of 3.0 is derived, a patented variety Jersey Centennial U.S. Plant Pat. No. 4,998 is obviously better than the Mary Washington at a rating of 5.0 whereas the variety of the instant invention, designated 277C×22-8 provides a rust rating of 5.4.

The summary is noted below.

"RUST RATINGS OF HYBRIDS PLANTED ON FUSARIUM LAND"

| | | | Rust Ratings[1] |
|---|---|---|---|
| A | New | 277C × 22-8 | 5.4 |
| B | Control | Jersey Centennial PP4998 | 5.0 |
| C | Control | Mary Washington | 3.0 |

[1]Rating 9 = Healthy; 1 = Very rusty, September 1985

Hybrid yellow of our new asparagus plant set forth in the table following, wherein control varieties Jersey Centennial U.S. Plant Pat. No. 4,998 and the unpatented variety Mary Washington are shown in the table as compared with the instant hybrid "Jersey Knight" are numeral designation 277C×22-8.

From this it will be observed that the jumbo and total marketable spears are vastly increased with this new hybrid as compared with the others, no attempt being made to supply information with regard to all varieties tested but sufficient to indicate the improvement provided hereby.

| | Jumbo[1] | | | Total Marketable[2] | | |
|---|---|---|---|---|---|---|
| | 1985[3] kg/ha | 1986[4] kg/ha | Total kg/ha | 1985[3] kg/ha | 1986[4] kg/ha | Total kg/ha |
| 277C × 22-8 | 124 | 273 | 397 | 841 | 2143 | 2984 |

-continued

| | Jumbo[1] | | | Total Marketable[2] | | |
|---|---|---|---|---|---|---|
| | 1985[3] kg/ha | 1986[4] kg/ha | Total kg/ha | 1985[3] kg/ha | 1986[4] kg/ha | Total kg/ha |
| 277E × 22-8 | 64 | 97 | 161 | 489 | 1157 | 1646 |
| 362M × 22-8 | 213 | 484 | 697 | 1010 | 2141 | 3151 |
| 382B × 22-8 | 110 | 34 | 144 | 679 | 1388 | 2067 |
| Jersey Cent. | 76 | 191 | 267 | 612 | 1330 | 1942 |
| Mary Washing. | 36 | 33 | 69 | 294 | 493 | 787 |

[1]Larger than 10/16" diameter, 9" spears
[2]Diameter 6/16" and larger, 9" spears
[3]First harvest season. Cut 4 weeks.
[4]Cut 6 weeks.

It is of course noted that in FIG. 1, from the table supplied and headed Asparagus Plant Data, as applied to the stalk, the various aspects of the stalk and flower as well as cladophyll data are applied to the drawing and are available for comparison with other varieties such as the patented variety Jersey Centennial U.S. Plant Pat. No. 4,998.

It may also be of value to note that the asparagus hybrid yields of plants in a commercial farm in New Jersey are summarized in a further table wherein the experimental hybrids so called are noted, the hybrid "Jersey Giant" the subject of U.S. Plant Pat. No. 5,551 is included in the listing as compared with our invention Jersey Knight, (277C×22-8) and a further control, unpatented variety Mary Washington.

This indicates that the Jumbo and Total Marketable spears yield of the instant variety are very satisfactory particularly as compared to Mary Washington. Total marketable weight is greater than "Jersey Giant" even though jumbo spear weight is not as great as "Jersey Giant" which is known good marketable variety.

ASPARAGUS HYBRID YIELD

| Hybrids | Jumbo lb/A | Total Marketable lb/A |
|---|---|---|
| Jersey Giant | 684 | 1059 |
| 277C × 22-8 | 588 | 1220 |
| Mary Washington | 113 | 196 |

It should be noted that in the above table the jumbo spears are those which are considered as larger than 10/16" in diameter, 9" long and the marketable spears 6/16" and larger of 9" spears.

ASPARAGUS PLANT DATA
ASPARAGUS PLANT NO. 277C × 22-8 "Jersey Knight"

| | |
|---|---|
| Stalk Data | |
| Number of nodes below first branch | 23 |
| Number of cm from crown to first branch | 55.9 |
| Number of branches | 63 |
| Number cm between first and last branch | 171.4 |
| Internode length in cm between branches | 2.72 |
| Number of cladophyll nodes beyond last branch | 33 |
| Number of cm beyond last branch | 21.0 |
| Internode length in cm beyond last branch | 0.64 |
| Note: All above are largest stalk. | |
| Largest stalk diameter in mm | 23.2 |
| Mean diameter of three largest stalks in mm | 22.1 |
| Number of stalks | 15 |
| Stalk vigor index (No. × (Mean Diam) | 7,326 |
| Mature stalk color, bloom removed. Color No. (1) | 22–14 |
| Highest headed stalk cm | 70.5 |
| Flower Data | |
| Petal tip (yellow) Color No. (1) | 25–3 |
| Petal base (purple) Color No. (1) | 46–8 |
| Flower length mm | 6.9 |
| Flower width at midpoint mm | 2.5 |
| Cladophyll Data | |
| Number per node | 4.50 |
| Length mm | 10.4 |
| Width mm | 0.102 |

From the foregoing tables and summaries as well as notations, it will be observed that our new "Jersey Knight" can be distinguished clearly from other asparagus plants in our program and certainly those existing in the market place as exemplified by Mary Washington.

We claim:

1. A new and distinct hybrid of asparagus plant as herein shown and described, characterized as to novelty by the unique combination of a male hybrid which has tolerance to rust (*Puccinia asparagi*), root rot (*Fusarium oxysporum*), and crown rot (*Fusarium moniliforme*), of substantially improved values, with a high yield of high quality spears, the spear tips remaining tight longer than those of standard cultivars and not opening when the spear is long being noticeably unaffected by hot weather, and substantially greater quantities of jumbo and marketable spears produced as compared with other varieties.

* * * * *